United States Patent [19]
Hoeger et al.

[11] Patent Number: 5,169,935
[45] Date of Patent: Dec. 8, 1992

[54] METHOD OF MAKING PEPTIDES

[75] Inventors: Carl A. Hoeger, San Marcos; Paula G. Theobald, Oceanside; John S. Porter, Leucadia; Jean E. F. Rivier, La Jolla, all of Calif.

[73] Assignee: The Salk Institute For Biological Studies, San Diego, Calif.

[21] Appl. No.: 541,810

[22] Filed: Jun. 20, 1990

[51] Int. Cl.$^5$ .................. A61K 37/02; C07K 5/00
[52] U.S. Cl. .................. 530/328; 530/333; 530/334; 525/54.11
[58] Field of Search .................. 530/328, 334, 333; 525/54.11

[56] References Cited

U.S. PATENT DOCUMENTS

| | | | |
|---|---|---|---|
| 4,043,992 | 8/1977 | Fujimoto et al. | 260/112.5 |
| 4,866,160 | 9/1989 | Coy et al. | 530/313 |
| 4,935,491 | 6/1990 | Folkers et al. | 530/313 |

OTHER PUBLICATIONS

Stewart et al., Solid Phase Peptide Syntheses (and ed 1984) 4-20.
Hocart et al. J. Med. Chem. vol. 30 No. 10 (1987) 1910-1914.
Hocart et al. CA107:134666h (1987).
Hocart et al. CA106:120222c (1987).
Bodanszky, Int'l. J. Peptide Res. 25, (1985) 449-474.

Primary Examiner—Merrell C. Cashion, Jr.
Assistant Examiner—B. Celsa
Attorney, Agent, or Firm—Fitch, Even, Tabin & Flannery

[57] ABSTRACT

Methods for making peptides of a suitable length for solid phase synthesis, which peptides include in their sequence a pair of residues of a different character which have acylated side chains and a residue which has an N-alkylated side chain. A peptide intermediate is constructed on the resin using commercially available starting materials. The N-terminus can be acylated by removing the α-amino protecting group and acylating under standard conditions. First primary amino protecting groups included in those residues to be acylated are removed, and acylation is effected, preferably by using a carboxypyridine or a similar heterocyclic acylating agent. Following such side chain acylation, a second protecting group included in the residue to be N-alkylated is removed, and the N-alkylation reaction is carried out while the peptide remains on the resin using a borohydride and an appropriate aldehyde or ketone. Following cleavage from the resin and removal of any protecting groups still remaining, the peptide is appropriately purified, thus requiring only a single purification to be carried out while forming a synthetic peptide including residues for which the modified amino acids are not readily commercially available.

2 Claims, No Drawings

METHOD OF MAKING PEPTIDES

This invention was made with Government support under Grant No. HD-13527 and Contract Nos. NO1-HD-9-2903 and NO1-HD-0-2906 awarded by the National Institutes of Health. The Government has certain rights in this invention.

This invention relates generally to the making of synthetic peptides and, more particularly, to the solid-phase synthesis of peptides having certain acylated side chains.

BACKGROUND OF THE INVENTION

The hypothalamic hormone GnRH (sometimes referred to as LH-RH or as LRF) which triggers the release of the gonadotropic hormones, particularly LH and FSH, was isolated over 15 years ago and characterized as a decapeptide having the structure:

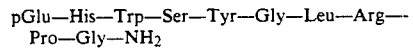

Peptides are compounds which contain two or more amino acids in which the carboxyl group of one acid is linked to the amino group of the other acid. The formula for GnRH, as represented above, is in accordance with conventional representation of peptides where the amino terminus appears to the left and the carboxyl terminus to the right. The position of an amino acid residue is identified by numbering the amino acid residues from left to right. In the case of GnRH, the hydroxyl portion of the carboxyl group of glycine at the C-terminus has been replaced with an amino group(NH₂) i.e. the C-terminus is amidated. The abbreviations for the individual amino acid residues above are conventional and are based on the trivial name of the amino acid, e.g. pGlu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Har is homoarginine, Pro is proline, Sar is sarcosine, Phe is phenylalanine, Ala is alanine, Val is valine, Nva is norvaline, Ile is isoleucine, Thr is threonine, Lys is lysine, Hly is homolysine, Asp is aspartic acid, Asn is asparagine, Gln is glutamine, and Met is methionine. Except for glycine, amino acids of the peptides described herein should be understood to be of the L-configuration unless noted otherwise.

There are reasons for desiring to prevent ovulation in female mammalians, and the administration of GnRH analogs that are antagonistic to the normal function of GnRH have been used to suppress or delay ovulation. For this reason, analogs of GnRH which are antagonistic to GnRH are being investigated for their potential use as contraceptives or for regulating conception periods. GnRH antagonists may also be used for the treatment of precocious puberty and endometriosis. Such antagonists have also been found useful to regulate the secretion of gonadotropins in male mammals and can be employed to arrest spermatogenesis, e.g. as male contraceptives for treatment of male sex offenders, and for treatment of prostatic hypertrophy. More specifically, GnRH antagonists can be used to treat steroid-dependent tumors, such as prostatic and mammary tumors. In the female, they can also be used for hirsutism.

A number of analogs of GnRH which have been synthesized showed high biological potency in inhibiting the secretion of the gonadotropins, such as those described and claimed in U.S. Pat. No. 4,444,759 issued Apr. 24, 1984 to Rivier and Vale. However, subsequent testing of such GnRH antagonists found that they also exhibited the undesirable side effect of causing the release of relatively large amounts of histamine, which could cause edema of the face and extremities. These overall effects of such synthetic analogs were reviewed in an article by Karten and Rivier which appeared in *Endocrine Reviews*, 7, pp. 44-66 (Feb. 1986).

Because it was felt that such side effects would likely prevent administering such antagonists to humans, other GnRH antagonist designs were sought. Cyclic GnRH antagonists are shown in U.S. Pat. No. 4,661,472 issued Apr. 28, 1987, and GnRH antagonists having the side chain of D-Glu or a similar residue in the 6-position modified (for example to form D-4-p-methoxybenzoyl-2-amino butyric acid) are shown in U.S. Pat. No. 4,677,193, issued Jun. 30, 1987.

Another proposal of investigators was to modify the D-Arg residue in the 6-position by substituting its guanadino side chain with alkyl groups, as shown in the article by Nestor, et al. *Peptides* 88, pp. 592-594. In an article by Rivier, et al., entitled GnRH Antagonists: N-Alkylation of Primary Amino Functions Generate New Potent Analogs, *Coll. Soc. Fr. Etudes Fertil.* (1988) 26, pp. 25-31, there is described the design and synthesis of potent GnRH antagonists which use N-alkylated lysine residues in the 6- and/or 8-positions.

Published International Application WO89/01944 discloses a series of decapeptide analogs of GnRH which have antagonistic properties and which release only low amounts of histamine; one of these compounds, termed Antide, utilizes NicLys in the 5-position and D-NicLys in the 6-position. By Nic is meant the acyl group nicotinoyl or 3-pyridylcarbonyl. Such GnRH antagonists appear to have commercial possibilities; however, the synthesis of these compounds is timestaking and relatively expensive. p-Nitrophenol nicotinate is first prepared by the reaction of nicotinic acid with nitrophenyl; it must then be precipitated, recrystallized and checked for purity and identity. This active ester is then reacted with lysine protected by Boc using a reaction that takes 36 hours, the product must again be recovered, recrystallized and checked for identity and purity. The resultant compound is then utilized as a part of a step-by-step solid phase synthesis of the decapeptide as is well known in the art. In order to make such decapeptides more readily available, it was felt that more efficient syntheses would be highly desirable.

SUMMARY OF THE INVENTION

It has been found that peptides which include a number of residues having different labile side chain groups, including modified primary amino groups, can be efficiently synthesized by acylating one or more side chain primary amino groups and by optionally alkylating another such side chain amino while the peptide or peptide fragment containing the residues in question remains attached to the insoluble resin employed in solid-phase synthesis. More particularly, the primary amino side chains are protected with a base-labile (or a hydrazine-labile or a thio-labile) protecting group that is not removed when the mild acid-labile protecting group (preferably Boc) is removed from the alpha-amino group at the end of each step of the solid phase synthesis. Following removal of the base-labile protecting groups, simultaneous acylation can be carried out of both L-isomer and D-isomer residues of lysine, or the like, to produce a desired peptide. Optionally, following removal of an acid-labile protecting group on another residue of Lys or the like, an N-alkylation can be carried out while the peptide remains attached to the insoluble resin support. Thereafter, following cleavage, purification is simply carried out as a part of the normal solid phase purification of the decapeptide, eliminating the need for additional and timestaking steps along the way.

DETAILED DESCRIPTION OF THE PREFERRED EMBODIMENTS

The fundamental premise of solid-phase peptide synthesis is that amino acids are assembled, generally one by one, into a peptide of a desired sequence while the amino acid residue that forms the carboxyl terminus of the peptide remains anchored to an insoluble support. Following the achievement of the completed sequence of residues on the resin support, a reagent is used to cleave the peptide chain from the support and liberate the completed peptide to solution. During the step-by-step buildup, the individual amino acids will often have side-chain protection for the labile groups, and these will remain in the completed form on the resin. Preferably, it is advantageous to remove the side chain protecting groups at the same time as the peptide is cleaved from the resin. Moreover, when particular resins are employed, peptides having C-terminal, N-substituted amides can be obtained upon cleavage from the resin, as taught in U.S. Pat. No. 4,569,967, the disclosure of which is incorporated herein by reference.

The present invention utilizes the selective removal of protecting groups from side chain primary amino groups of the peptide that has been built up on a resin support and the acylation of the free amino side chains while a part of the peptidoresin. The method is particularly advantageous in being able to simultaneously acylate both L-isomers and D-isomers that may be included in a particular peptide chain and in avoiding the need for separate purification steps to create peptides having side chains acylated with unusual acylating agents, for example, nicotinic acid and its isomers, i.e. the carboxypyridines. Following such an acylation step and removal of the remaining side chain protecting groups (or at least the protecting group on another residue having a side-chain primary amino group), an N-alkylation of that group can be carried out before cleavage from the resin. Generally, commonly commercially available, protected amino acids can be employed in the solid-phase synthesis, peptide-building reactions, and a multitude of individual purifications are not necessary as the standard purification of the decapeptides or the like, following solid-phase synthesis, may be employed.

Because the entire peptide can be completed prior to the acylation of the desired side chains, more than one final peptide can be created from the preparation of a single peptidoresin batch, as the batch can be split into two or more parts following the completion of the peptide chain before carrying out the acylation reaction, permitting different portions to be treated with different acylating agents in order to produce different GnRH analogs. Furthermore, the employment of this particular synthesis allows acylation of the N-terminus of the peptide, if desired, to be effected on the resin prior to the removal of the side-chain protecting groups under conditions such that the reaction proceeds readily and the yields are high. As mentioned above, the synthesis is considered to be particularly advantageous when two residues of a different character in the same peptide chain, as for example a D-isomer and an L-isomer, require acylation, and even more particularly when that chain contains a residue that is N-alkylated.

The method is considered to be useful in the synthesis of a peptide of any length that would normally be considered suitable for synthesis by solid phase synthesis procedures, for example peptides between about 5 and about 50 residues in length. At the present time, the invention is considered to be particularly advantageous to synthesize antagonists of GnRH which are decapeptide or nonapeptide analogs of this native hormone. Such antagonists are useful to strongly inhibit the secretion of gonadotropins by the pituitary gland of humans or the like, and also inhibit the release of steroids by the gonads. The peptides of particular current interest are analogs of GnRH containing an L-isomer in the 5-position having an acylated primary amino side chain and a D-isomer in the 6-position also having an acylated primary amino side chain; they may also have an N-alkylated residue in the 8-position.

Although the remainder of such a molecule can be formed with residues having a fairly wide latitude of selection, as a result of design and testing over the last decade, there are some present preferences for the residues in these positions--which are for the most part substitutions from those which appear in the native hormone. For example, a GnRH antagonist should have a 1-position substitution, preferably dehydroPro or β-(1-or 2-naphthyl)-D-alanine (hereinafter β-D-1NAL or β-D-2NAL), a 2-position substitution in the form of a modified D-Phe and a 3-position substitution, preferably in the form of substituted or unsubstituted D-Trp, D-3PAL or β-D-NAL. The 5-position is occupied by Lys or another α-amino acid having a primary amino side chain in which the side chain amino group is acylated by a desired acylating agent, such as a carboxypyridine, i.e. Lys(cpd), preferably Lys(3cpd), which is called nicotinic acid and also referred to as Lys(Nic), and the 6-position is occupied by a similarly acylated D-isomer. Instead of Leu in the 7-position, one of the following residues may be present: Nle, NML, Phe, Nva, Met, Tyr, Trp or PAL, of which Phe or Trp may be substituted. The 8-position is preferably isopropyl Lys, i.e., (ILys) or Lys(Ipr), wherein the side chain amino group is akylated by isopropyl, and D-Ala is preferably present in the 10-position.

Modified D-Phe in the 2-position provides increased antagonistic activity as a result of specific modifications present in the benzene ring. Single substitutions for hydrogen in the ring are preferably made in the para- or 4-position, but might also be in either the 2- or 3-position; the substitutions are selected from chloro, fluoro, bromo, methyl, methoxy and nitro, with chloro, fluoro and nitro being preferred. Dichloro substitutions may be made in the 2,4 or 3,4 positions in the ring. The α-carbon atom may also be methylated, e.g. ($C^α$-Me/4Cl)Phe. The 1-position substituent is preferably modified so that its α-amino group contains an acyl group, such as formyl(For), acetyl(Ac), acrylyl(Acr), vinylacetyl(Vac) or benzoyl(Bz), with acetyl and acrylyl being preferred. PAL and D-PAL represent the L- and D-isomers of pyridylalanine where the β-carbon of Ala is linked to the 2-, 3- or 4-position, preferably to the 3-position, on the pyridine ring.

The following formula is generally indicative of one class of peptides that can be advantageously synthesized by the invention:

G—AA$_1$—(A')D—
Phe—AA$_3$—Ser—AA$_5$—AA$_6$—AA$_7$—AA$_8$—
Pro—AA$_{10}$ wherein G is hydrogen or an acyl group having 7 or less carbon atoms; AA$_1$ is dehydroPro, (A)D-Phe, (B)D-Trp, Pro, or β-D-NAL; (A) is H, Cl, F, NO$_2$, CH$_3$, OCH$_3$, C$^a$Me/4Cl, Cl$_2$ or Br; (B) is H, NO$_2$, NH$_2$, OCH$_3$, F, Cl, Br, CH$_3$, N$^{in}$For or N$^{in}$Ac; A' is Cl, F, NO$_2$, CH$_3$, OCH$_3$, C$^a$Me/4Cl, Cl$_2$ or Br; AA$_3$ is D-PAL, β-D-NAL or (B)D-Trp; AA$_5$ is (C)Lys, (C)Orn, (C)Dbu, (C)Hyl or (C)Dpr; (C) is an acyl group; AA$_6$ is (C)D-Orn, (C)D-Lys, (C)D-Dbu, (C)D-Hyl or (C)D-Dpr; AA$_7$ is Nle, Leu, NML, (A)Phe, Met, Nva, Tyr, (B)Trp or PAL; AA$_8$ is ILys, (D)Arg or (D)Har; (D) is H or di-lower alkyl; AA$_{10}$ is D-Ala-NH$_2$, Gly-NH$_2$, NHNHCONH$_2$ or NH(R); R is lower alkyl.

By dehydroPro is meant 3,4 dehydroproline, C$_5$H$_7$O$_2$N. By β-D-NAL is meant the D-isomer of alanine which is substituted by naphthyl on the β-carbon atom, i.e., also 3-D-NAL. Preferably β-D-2NAL is employed wherein the attachment to naphthalene is at the 2-position on the ring structure; however, β-D-1NAL may also be used. PAL represents alanine which is substituted by pyridyl on the β-carbon atom; preferably the linkage is to the 3-position on the pyridine ring. When substituted D-Trp is employed, single substitutions for hydrogen are preferably made in either the 5- or 6-position, which are selected from chloro, fluoro, bromo, methyl, amino, methoxy and nitro, with chloro, fluoro and nitro being preferred. Alternatively, the indole nitrogen may be acylated, e.g. with formyl (N$^{in}$-For-or 1For-) or with acetyl. N$^{in}$For-D-Trp and 6NO$_2$-D-Trp are the preferred substituted residues. By NML is meant N$^a$CH$_3$-L-Leu. By Dbu is meant alpha, gamma diamino butyric acid, and by Dpr is meant α, β diamino propionic acid. By AzaGly-NH$_2$ is meant NHNHCONH$_2$. The guanidino group of an Arg residue optionally present in the 8-position may be substituted by lower alkyl, i.e. 1 to about 4 carbon atoms, e.g., propyl(Pr). D-Lys, D-Dbu, D-Dpr, D-Hyl or D-Orn is present in the 6-position, and its side-chain-amino group is acylated by a heterocyclic acyl group, e.g. nicotinic acid.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation- or chemotherapy. They are also useful for treatment of steroid-dependent tumors. Effective dosages will vary with the form of administration and the particular species of mammal being treated. An example of one typical dosage form is a bacteriostatic water solution containing the peptide which solution is administered parenterally to provide a dose in the range of about 0.1 to 2.5 mg/kg of body weight per day.

Peptides are synthesized using solid phase techniques in accordance with the present invention. A chloromethylated resin or a hydroxymethylated resin is generally used for peptides either having a free acid C-terminus or having AzaGly-NH$_2$ in the 10-position. A methylbenzhydrylamine(MBHA) resin, a benzhydrylamine (BHA) resin or some other suitable resin known in the art is used when a C-terminal amide or substituted amide is desired for such is directly provided upon cleavage. For example, peptides having a substituted amide at the C-terminus are preferably synthesized using an N-alkylamino methyl resin as taught in U.S. Pat. No. 4,569,967, issued February phase synthesis is conducted in a manner to stepwise add the amino acids in the chain in the manner set forth in detail in the U.S. Pat. No. 4,211,693. Side-chain protecting groups, as are well known in the art, are preferably a part of the amino acids employed in the synthesis when particularly labile side chains are present, and they may optionally be used as a part of others, such as Trp. The result of such synthesis is the creation of the fully protected intermediate peptidoresin.

As previously indicated, the invention is useful for making peptides of substantially any length that are normally synthesized by solid-phase synthesis. To illustrate the invention with respect to making GnRH antagonists, chemical intermediates in accordance with the following formula are considered to be representative of those which would be created as a part of such a method: X$^1$-AA$_1$-(A')D-Phe-AA$_3$(X$^2$)-Ser(X$^3$)-AA$_5$(X$^6$)-AA$_6$(X$^6$)-AA$_7$(X$^2$ or X$^4$)-AA$^8$(X$^5$ or X$^7$)-Pro-X$^8$ wherein: X$^1$ is an α-amino protecting group of the type known to be useful in the art in the stepwise synthesis of polypeptides and when G in the desired peptide composition is a particular acyl group, that group may be used as the protecting group. Among the classes of α-amino protecting groups covered by X$^1$ are (1) acyl-type protecting groups, such as formyl(For), trifluoroacetyl, phthalyl, p-toluenesulfonyl(Tos), benzoyl(Bz), benzenesulfonyl, dithiasuccinoyl(Dts) o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxycarbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc when X is hydrogen.

X$^2$ is hydrogen or a protecting group for the indole nitrogen of Trp, such as Bz, Ac or For. In many syntheses there is no need to protect Trp, and such protection is not used if acylated D-Trp is present elsewhere in the peptide.

X$^3$ is a protecting group for the hydroxyl side chain of Ser e.g. Ac, Bz, trityl, DCB or benzyl ether(Bzl) and is preferably Bzl.

X$^4$ is hydrogen or a protecting group for the phenolic hydroxyl group of Tyr selected from the group consisting of tetrahydropyranyl, tert-butyl, trityl, benzyl, Z, 2-bromobenzyloxycarbonyl(2BrZ) and 2,6-dichlorobenzyl(DCB). 2BrZ is preferred.

$X^5$ is a protecting group for a side chain guanidino group, such as that in Arg or Har, or for the imidazole group of His, such as nitro, Tos, trityl, adamantyloxycarbonyl, Z and 2,4-dinitrophenol(Dnp), or $X^5$ may be hydrogen, which means there is no protection on the side chain group atoms. Tos is generally preferred.

$X^6$ is a protecting group for an amino side chain group that can be removed without removing other side chain protecting groups so as to allow the omega-amino group to thereafter be acylated without affecting the other amino-acid residues. Preferably a base-labile group, such as Fmoc, methylsulfonylethyloxycarbonyl(Msc) or trifluoroacetyl(Tfa), is used; however, it may also be possible to use a hydrazine-labile group such as phthaloyl, or a thiolabile group such as Nps or Dts.

$X^7$ is a protecting group for an amino side-chain group that is not removed upon removal of $X^6$, e.g. it may be an acid-labile group, such as Z or 2ClZ, or it may be a thiol- or hydrazine-labile group when $X^6$ is base-labile, for example.

$X^8$ may be Gly-OCH$_2$-[resin support],-OCH$_2$-[resin support], Gly-NH-[resin support], D-Ala-NH-[resin support]or N(A)-[resin support]. Although Met may be protected, as by oxygen; Met is generally left unprotected.

The criterion for selecting side chain protecting groups for $X^2$-$X^5$ is that the protecting group should be stable to the reagent under the reaction conditions selected for removing the o-amino protecting group (preferably Boc) at each step of the synthesis and for removing the $X^6$ groups. Protecting groups generally should not be split off under coupling conditions but should be removable upon completion of the synthesis of the desired amino acid sequence under reaction conditions that will not alter the peptide chain.

When the $X^8$ group is Gly-OCH$_2$-[resin support], or OCH$_2$-[resin support], the ester moiety of one of the many functional groups of the polystyrene resin support is being represented. When the $X^8$ group is Gly-NH-[resin support] or D-Ala-NH-[resin support], an amide bond connects Gly or D-Ala to a BHA resin or to a MBHA resin. When the $X^8$ group is N(A)-[resin support], a substituted amide bond connects Pro to an N-alkylaminomethyl (NAAM) resin.

When G is acetyl, for example, in the final formula, it may be possible to employ it as the $X^1$ protecting group for the α-amino group of β-D-NAL or whatever amino acid is used in the 1-position by adding it before coupling this last amino acid to the peptide chain. However, a reaction is preferably carried out with the peptide on the resin (after deblocking the α-amino group while the side-chain groups remain protected), e.g. by reacting with acetic acid, in the presence of dicyclohexyl carbodiimide (DCC), or preferably with acetic anhydride or by another suitable reaction as known in the art.

Thus, in one aspect, the invention more specifically provides a method for making a peptide having the formula: G-AA$_1$-(A')D-Phe-AA$_3$-Ser-AA$_5$-AA$_6$-AA$_7$-AA$_8$-Pro-AA$_{10}$ wherein the symbols are as set forth hereinbefore, which method comprises (a) forming an intermediate peptide having the formula: $X^1$-AA$_1$-(A')D-Phe-AA$_3$(X$^2$)-Ser(X$^3$)-AA$_5$(X$^6$)-AA$_6$(X$^6$)-AA$_7$(X$^2$ or X$^4$)-AA$_8$(X$^5$ or X$^7$)-Pro-X$^8$ wherein $X^1$ is hydrogen or an α-amino protecting group; $X^2$ is hydrogen or a protecting group for an indole nitrogen; $X^3$ is a protecting group for a hydroxyl group of Ser; $X^4$ is hydrogen or a protecting group for a phenolic hydroxyl group of Tyr; $X^5$ is either hydrogen or a protecting group for a guanidino or imidazole group; $X^6$ is a protecting group for a primary amino group that is base-labile, hydrazine-labile or thio-labile; $X^7$ is a protecting group for a primary amino group that is not removed upon removal of $X^6$; $X^8$ is Gly-OCH$_2$-[resin support], OCH$_2$-[resin support], Gly-NH-[resin support], D-Ala-NH-[resin support], or N(A)-[resin support], (b) removing said $X^6$ protecting groups to deprotect side chain primary amino groups on residues AA$_5$ and AA$_6$ of said intermediate peptide; (c) reacting said deprotected side chain primary amino groups with an acylating agent; and (d) splitting off any remaining groups $X^1$ to $X^7$, optionally N-alkylating a residue having a side chain formerly protected by $X^7$, and cleaving from the resin support included in $X^8$ and (e) optionally reacting the free peptide to form an acid addition salt or the like.

Purification of the peptide is effected by ion exchange chromotography on a CMC column, followed by partition chromatography using the elution system: n-butanol;0.1 N acetic acid (1:1 volume ratio) on a column packed with Sephadex G-25, or by using HPLC, as known in the art and specifically set forth in J. Rivier, et al. *J. Chromatography*, 288 (1984) 303-328.

These antagonists are effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.1 to about 2.5 milligrams per kilogram of body weight. These analogs are particularly soluble at physiological pHs and thus can be prepared as relatively concentrated solutions for administration. The antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

As explained generally hereinbefore, two side-chain protected residues are incorporated in the main peptide chain, for example Lys and D-Lys; Orn, Dbu, Hly or Dpr and a D-isomer thereof; or an L-isomer of one and a D-isomer of a different amino acid, employing protecting groups which permit their deprotection without deprotecting the rest of the side chains. The deprotected primary amino groups are then acylated while the peptide chain is still attached to the resin support. As explained in more detail hereinafter, following deprotection of another such residue, an N-alkylation reaction can be performed with the peptidoresin.

The acylating agent that is employed is of course dependent upon the structure of the ultimate peptide that is desired; however, generally any appropriate carboxylic acid might be employed in the overall method of the invention, e.g. acetic acid, propionic acid, butyric acid, etc. When GnRH antagonists are being formed and it is desired to add a heterocyclic acyl group to a side chain amino group in the 5- and/or 6-position, acylating agents such as indole acetic acid, imidazole acetic acid and carboxytriazole; however the preferred acylating agents are those selected from the following group: carboxypyridine, substituted carboxypyridine, carboxypyrimidine, substituted carboxyprimidine, carboxypyrazine and substituted carboxypyrazine. When there is a substitution, it is preferably chloro, nitro, amino, thio, lower alkylthio, hydroxy, lower alkoxy, aryl or lower alkyl, having 1 to 6 carbon atoms and most preferably methyl or ethyl. For example, 3-carboxypyridine (nicotinic acid) may be preferred; however, 2-carboxypyridine (picolinic acid) or 4-carboxypyridine (isonicotinic acid) may be used. When a substituted carboxypyridine is employed, a methyl or ethyl substitution preferably appears in the 6-position. When a carboxypyrimidine is employed as the acylating agent, preferably 4-carboxypyrimidine is used, and if substituted by methyl, for example, the substitution is preferably in the 2- or in the 6-position. If a carboxypyrazine is employed, preferably 3-carboxypyrazine is employed, and if it is substituted, as by methyl, the substitution is preferably made in the 6-position.

A more preferred group of acylating agents are those having the formula:

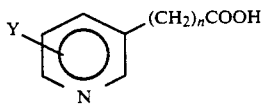

wherein n is an integer from 0 to 10 and preferably is 0, 1 or 2 and wherein Y is Cl, $NO_2$, $NH_2$, SH, SR', OH, OR', or R', with R' being lower alkyl or aryl.

As mentioned above, if the N-terminus of the peptide is to be acylated, the acylation reaction is preferably carried out prior to the removal of the side chain protecting groups on the primary amino side chains. This allows flexibility in performing the N-terminal acylation, allowing it to be carried out in a manner such as not to detract from overall yield. Following such acylation if N-terminal acylation is carried out, the groups protecting the primary amino side chains in the 5-and the 6-positions are then appropriately removed without removing the acid-labile groups that are protecting the other labile side chains in the peptide sequence. Once removed, the free amino groups are then reacted with the acylating agent in a suitable solvent, such as DMF in the presence of the usual amount of a coupling agent such as DCC (dicyclohexylcarbodiimide) or DIIC (diisopropylcarbodiimide). A reasonably large excess of the acylating agent is preferably used, for example, 5 to 10 times the molar amount. The reaction proceeds readily at room temperature, and it is complete after about one to two hours.

When N-alkylation of the side chain of another residue in the amino acid sequence of the peptide that has been synthesized is desired, this residue (or residues) has the primary amino group of its side chain protected by a protecting group that is not removed during the removal of the protecting groups from those residues to be acylated. When synthesizing the illustrated decapeptides or nonapeptides, it is convenient and preferable to protect a residue to be N-alkylated with an acid-labile protecting group, such as Z or 2ClZ,—on the premise that there are no other labile side chains that would partake in the N-alkylation reaction in such a sequence. However, if desired, the residue or residues to be acylated might be protected by a base-labile protecting group while the residue or residues to be N-alkylated are protected by a thio-labile or hydrazine-labile protecting group, or vice versa. An acid-labile protecting group such as 2ClZ can be efficiently removed by phase transfer hydrogenation which will also remove the remaining protecting groups such as those on the serine residue and on a Tyr or Trp residue, if present. It is preferably carried out using a palladium catalyst on charcoal in the presence of cyclohexane or a similar donor molecule, with the reaction proceeding readily at room temperature and being complete in about two hours. Following washing of the peptidoresin, the N-alkylation reaction is carried out using a borohydride and an appropriate carbonyl compound. For example, the reaction with $NaBH_4$ and acetone proceeds readily at room temperature, and isopropylation is complete in two hours. Thereafter, the peptidoresin is subjected to the standard wash, and then the peptide is cleaved from the resin support under standard conditions.

If an optional N-alkylation step is not carried out, the still-protected peptide may be cleaved from the resin and either simultaneously or subsequently deprotected to remove the remaining side chain protecting groups. Preferably deprotection of the peptide and cleavage of the peptide from a resin support are accomplished using HF at a temperature of about 0° C. or slightly above, although the conclusion of such cleavage can be carried out at room temperature. Anisole is preferably added to the peptidoresin prior to treatment with HF. After removal of HF under vacuum, the cleaved, deprotected peptide is conveniently treated with ether, decanted, taken up in dilute acetic acid and lyophilized. It is finally purified using standard procedures.

The following examples illustrate presently preferred methods for carrying out the invention and should be understood to be illustrative of, but not limiting upon, the scope of the invention which is defined in the appended claims.

EXAMPLE I

The peptide [Ac-β-D-2NAL$^1$, (4Cl)D-Phe$^2$, D-3PAL$^3$, Lys(Nic)$^5$, D-Lys(Nic)$^6$, ILys$^8$, D-Ala$^{10}$]-GnRH is prepared by solid phase synthesis. This peptide has the following formula: Ac-β-D-2NAL-(4Cl)D-Phe-D-3PAL-Ser-Lys(nicotinoyl)-D-Lys (nicotinoyl)-Leu-Lys(isopropyl)-Pro-D-Ala-NH$_2$.

An MBHA resin is used, and Boc-protected D-Ala is coupled to the resin over a 2-hour period in $CH_2Cl_2$ using a 3-fold excess of Boc derivative and DCC as an activating reagent. The D-Ala residue attaches to the MBHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | Isopropyl alcohol + 1% ethanedithiol wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. | 30-300 |

-continued

| STEP | REAGENTS AND OPERATIONS | MIX TIMES MIN. |
|------|-------------------------|----------------|
|      | of either dimethylformamide (DMF) or CH$_2$Cl$_2$, depending upon the solubility of the particular protected amino acid, (1 time) plus DCC (10 mmoles) in CH$_2$Cl$_2$ |   |
| 10   | MeOH wash-40 ml. (2 times) | 3 |
| 11   | Triethylamine (TEA) 12.5 percent in CH$_2$Cl$_2$-70 ml. (1 time) | 3 |

After step 3, an aliquot may be taken for a ninhydrin test as well known in the art: if the test is negative, proceed to step 4 for removal of Boc-group prior to coupling of the next amino acid; if the test is positive or slightly positive, repeat steps 9 through 11.

The above schedule is used for coupling of each of the amino acids of the peptide of the invention after the first amino acid has been attached. N$^\alpha$Boc protection is used for each of the remaining amino acids throughout the synthesis. N$^\alpha$Boc-$\beta$-D-2NAL is prepared by a method known in the art, e.g. as described in detail in U.S. Pat. No. 4,234,571, issued Nov. 18, 1980, or the commercially available compound is obtained from Synthetech, Oregon, U.S.A. The side chains of Lys in the 5-position and of D-Lys in the 6-position are protected with Fmoc. Bzl is used as a side chain protecting group for the hydroxyl group of Ser. Boc-Lys(Ipr) is used for the 8-position. After deblocking the $\alpha$-amino group at the N-terminus using trifluoroacetic acid(TFA), acetylation of the N-terminus is achieved using a large excess of acetic anhydride in dichloromethane.

Following completion of the assembly of the peptide and acetylation of the N-terminus, the following intermediate is present: Ac-$\beta$-D-2NAL-(4Cl)D-Phe-D-3PAL-Ser(Bzl)-Lys(Fmoc)-D-Lys(Fmoc)-Leu-Lys-(Ipr)-Pro-D-Ala-NH-[MBHA resin support]. The side chains of the lysine residues in the 5- and 6-positions are simultaneously acylated by carrying out the following reactions. The Fmoc protecting group is removed from both by treatment of the peptidoresin with 20 percent piperidine in DMF for 5 minutes, washing with DMF, and then treating with more piperidine/DMF for 25 minutes. Completion of this step assures total removal of the Fmoc protecting groups. After washing the resin with DMF, CH$_3$OH, CH$_2$Cl$_2$, and finally DMF, the newly freed amino groups are treated with an excess (about 28 mmoles) of nicotinic acid (Niacin, from Calbiochem) in DMF, using DIIC (28 mmoles) as a coupling agent. Thereafter, the peptide is then subjected to the standard wash (see Steps 10–11).

The cleavage of the peptide from the resin and deprotection of the Ser side chain takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by high performance liquid chromatography (HPLC), as known in the art and specifically set forth in J. Rivier, et al. *J. Chromatography.* 288 (1984) 303–328.

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain; mass spectral analysis is also consistent. The optical rotation is measured on a photoelectric polarimeter as $$[\alpha]_D^{20} = -29.5 \pm 0.5 \ (c = 1, 50\% \text{ acetic acid}).$$

The peptide is assayed in vitro using dissociated rat pituitary cells maintained in culture for 4 days prior to the assay. The levels of LH mediated in response to the application of the peptide is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i.e. [Ac-dehydro Pro$^1$, (4F)D-Phe$^2$, D-Trp$^{3,6}$]-GnRH or the test peptide, in concentrations ranging from 0.01 to 10 nanomolar. The amount of LH secreted in the samples treated only with GnRH is compared with that secreted by the samples treated with the peptide plus GnRH. The ability of the test peptide to reduce the amount of LH released by 3 nanomolar GnRH is compared to that of the present standard peptide. Based upon this test, the peptide is considered effective to block GnRH-induced LH secretion in vitro at a relatively low concentration, such that it is assured that the synthesis resulted in formation of the correct compound, which is also termed Antide.

EXAMPLE II

The process of Example I is repeated to build nearly the same protected peptidoresin except that commercially available Boc-Lys(2ClZ) is used as the third amino acid added. Following removal of the Fmoc protecting groups, the peptidoresin is reacted with 3-carboxypyridine (nicotinic acid) in DMF, using DIIC as a coupling agent, under the same reaction conditions as set forth in Example I, which results in the synthesis of the peptide intermediate which has the following formula: Ac-$\beta$-D-2NAL-(4Cl)D-Phe-D-3PAL-Ser(Bzl)-Lys(nicotinoyl)-D-Lys(nicotinoyl)-Leu-Lys(2ClZ)-Pro-D-Ala-NH-[MBHA resin support].

The peptidoresin is then reacted with cyclohexane in the presence of a paladium catalyst on charcoal to accomplish phase transfer hydrogenation at the 2ClZ and Bzl protecting groups for about two hours at room temperature in DCM (dichloromethane) as a solvent. The resultant deprotected peptidoresin is washed, and it is then treated with about 100 millimoles of acetone to form a Schiff's base in a buffer solution of sodium borate at a pH of about 9 and treated with about 100 millimoles of sodium borohydride (NaBH$_4$) After about two hours at room temperature, the reaction mixture and the peptidoresin are separated, and the resin is treated with TFA at about 0° C. and then given the standard wash. Cleavage of the peptide from the resin and purification is then carried out under the same conditions as set forth in Example I. Following purification, the resultant peptide is compared with that obtained from Example I and found to be indistinguishable.

EXAMPLE III

The process of Example I is repeated to build precisely the same protected peptidoresin. Following removal of the Fmoc protecting groups, the peptidoresin is reacted with 2-carboxypyridine (picolinic acid) in DMF, using DIIC as a coupling agent, under the same reaction conditions as set forth in Example I, which results in the synthesis of the decapeptide [Ac-$\beta$-D-2NAL$^1$, (4Cl)D-Phe$^2$, D-3PAL$^3$, Lys(Pic)$^5$, D-Lys(-Pic)$^6$, ILys$^8$, D-Ala$^{10}$]-GnRH. This peptide has the following formula: Ac-$\beta$-D-2NAL-(4Cl)D-Phe-D-3PAL-Ser-Lys(picolinoyl)-D-Lys (picolinoyl)-Leu-Lys(isopropyl)-Pro-D-Ala-NH$_2$.

EXAMPLE IV

The process of Example I is repeated to build precisely the same protected peptidoresin. Following removal of the Fmoc protecting groups, the peptidoresin is reacted with 4-carboxypyridine (isonicotinic acid) in DMF, using DIIC as a coupling agent, under the same reaction conditions as set forth in Example I, which results in the synthesis of the decapeptide [Ac-$\beta$-D-2NAL$^1$, (4Cl)D-Phe$^2$, D-3PAL$^3$, Lys(INic)$^5$, D-Lys(INic)$^6$, ILys$^8$, D-Ala$^{10}$]-GnRH. This peptide has the following formula: Ac-$\beta$-D-2NAL-(4Cl)D-Phe-D-3PAL-Ser-Lys(isonicolinoyl)-D-Lys(isonicolinoyl)-Leu-Lys(isopropyl)-Pro-D-Ala-NH$_2$.

EXAMPLE V

The process of Example I is repeated to build precisely the same protected peptidoresin. Following removal of the Fmoc protecting groups, the peptidoresin is reacted with 3-carboxy-6-methyl-pyridine in DMF, using DIIC as a coupling agent, under the same reaction conditions as set forth in Example I, which results in the synthesis of the decapeptide [Ac-$\beta$-D-2NAL$^1$, (4Cl)D-Phez$^2$, D-3PAL$^3$, Lys(MNic)$^5$, D-Lys(MNic)$^6$, ILys$^8$, D-Ala$^{10}$]-GnRH. This peptide has the following formula: Ac-$\beta$-D-2NAL-(4Cl)D-Phe-D-3PAL-Ser-Lys(6-methylnicotinoyl) -D-Lys(6-methylnicotinoyl)-Leu-Lys(isopropyl) -Pro-D-Ala-NH$_2$.

EXAMPLE VI

The process of Example I is repeated to build precisely the same protected peptidoresin. Following removal of the Fmoc protecting groups, the peptidoresin is reacted with 4-carboxypyrimidine in DMF, using DCC as a coupling agent, under the same reaction conditions as set forth in Example I, which results in the synthesis of the decapeptide [Ac-$\beta$-D-2NAL$^1$, (4Cl)D-Phe$^{22}$, D-3PAL$^3$, Lys(Pmc)$^5$, D-Lys(Pmc)$^6$, ILys$^8$, D-Ala$^{10}$]-GnRH.

EXAMPLE VII

The process of Example I is repeated to build precisely the same protected peptidoresin. Following removal of the Fmoc protecting groups, the peptidoresin is reacted with 2-methyl-4-carboxypyrimidine in DMF, using DIIC as a coupling agent, under the same reaction conditions as set forth in Example I, which results in the synthesis of the decapeptide [Ac-$\beta$-D-2NAL$^1$, (4Cl)D-Phe$^{22}$, D-3PAL$^3$, Lys(MPmc)$^5$, D-Lys(MPmc)$^6$, ILys$^8$, D-Ala$^{10}$]-GnRH.

EXAMPLE VIII

The process of Example I is repeated to build precisely the same protected peptidoresin. Following removal of the Fmoc protecting groups, the peptidoresin is reacted with 3-carboxypyrazine in DMF, using DCC as a coupling agent, under the same reaction conditions as set forth in Example I, which results in the synthesis of the decapeptide [Ac-$\beta$-D-2NAL$^1$, (4Cl)D-Phe$^{22}$, D-3PAL$^3$, Lys(Pzc)$^5$, D-Lys(Pzc)$^6$, ILys$^8$, D-Ala$^{10}$]-GnRH.

EXAMPLE IX

The process of Example I is repeated to build precisely the same protected peptidoresin. Following removal of the Fmoc protecting groups, the peptidoresin is reacted with 2-carboxy-6-methylpyridine in DMF, using DCC as a coupling agent, under the same reaction conditions as set forth in Example I, which results in the synthesis of the decapeptide [Ac-$\beta$-D-2NAL:, (4Cl)D-Phe$^2$, D-3PAL$^3$, Lys(MPic)$^5$, D-Lys(MPic)$^6$, ILys$^8$, D-Ala$^{10}$]-GnRH. This peptide has the following formula: Ac-$\beta$-D-2NAL-(4Cl)D-Phe-D-3PAL-Ser-Lys(6-methylpicotinyl) -D-Lys(6-methylpicotinyl)-Leu-Lys(isopropyl)-Pro-D-AlaNH$_2$.

EXAMPLE X

The process of Example I is repeated to build precisely the same protected peptidoresin. Following removal of the Fmoc protecting groups, the peptidoresin is reacted with 3-carboxy-6-nitro-pyridine (6-nitronicotinic acid) in DMF, using DIIC as a coupling agent, under the same reaction conditions as set forth in Example I, which results in the synthesis of the decapeptide [Ac-$\beta$-D-2NAL$^1$, (4Cl)D-Phe$^2$, D-3PAL$^3$, Lys(NNic)$^5$, D-Lys(NNic)$^6$, ILys$^8$, D-Ala$^{10}$]-GnRH. This peptide has the following formula: Ac-$\beta$-D-2NAL-(4Cl)D-Phe-D-3PAL-Ser-Lys(6-nitronicotinoyl)-D-Lys(6-nitronicotinoyl)-Leu-Lys(isopropyl)-Pro-D-Ala-NH$_2$.

EXAMPLE XI

A peptide intermediate having the formula: Ac-$\beta$-D-2NAL-(4Cl)D-Phe-D-3PAL-Ser(Bzl)-Lys(Dts)-D-Lys(Dts)-NML-ILys-Pro-D-Ala-NH-[resin support] is prepared by the solid phase procedure generally referred to above. The intermediate is then treated to remove the Dts protecting groups from the amino side chains of the Lys residues using a suitable thiol, such as $\beta$-mercaptoethanol or thiophenol(PhSH), in DMF, and then reacted with nicotinic acid with DIIC as a coupling agent. Thereafter, the peptidoresin is given the standard wash. Deprotection and cleavage are then carried out as previously described. Following HPLC purification as previously described, the GnRH antagonist is tested and found to be the same as that synthesized in Example I.

EXAMPLE XII

A peptide intermediate having the formula: Ac-$\beta$-D-2NAL-(4Cl)D-Phe-D-Trp-Ser(Bzl)-Orn(Nps)-D-Lys(-Fmoc)-N!$\varepsilon$-Arg(Tos)-Pro-D-Ala-NH-[resin support] is prepared by the solid phase procedure referred to above. The peptide intermediate is first treated with a suitable thiol as described in Example XI to remove the Nps protecting group. It is then reacted with 2-benzyl-4-carboxypryidine in DMF with DCC as a coupling agent to acylate the Orn residue in the 5-position. After washing, the peptidoresin is treated with piperidine as in Example I to remove the Fmoc protecting group and then treated with nicotinic acid and DIIC to acylate the D-Lys residue in the 6-position. Following cleavage and HPLC purification as previously described, the GnRH antagonist is tested, and the peptide is considered to be effective to prevent ovulation of female mammals at low dosages.

EXAMPLE XIII

A peptide intermediate having the formula: Ac-dehydroPro-(4F)D-Phe-$\beta$-D-2NAL-Ser(Bzl)-Dbu(Fmoc)-D-Dbu(Fmoc)-Trp-Lys(2ClZ)-Pro-Gly-NH-[resin support] is prepared by the solid phase procedure referred to above. Following the removal of the Fmoc protection, the peptide intermediate is reacted as generally described in Example II, but using 6-amino-nicotinic acid instead of nicotinic acid to acylate the side chain amino groups of the Dbu and D-Dbu residues in the 5- and 6-positions, and then N-alkylating the 8-position Lys residue using Pd on charcoal and acetone after removal of the 2ClZ protecting group. Following cleavage and HPLC purification as previously described, the GnRH antagonist is tested, and the peptide is considered to be effective to prevent ovulation of female mammals at low dosages.

EXAMPLE XIV

A peptide intermediate having the formula: Ac-$\beta$-D-1NAL-(4Cl)D-Phe-(6NO$_2$)D-Trp-Ser(Bzl)-Dpr(Fmoc)-D-Dpr(Fmoc)-Tyr(2BrZ)-Lys(Ipr)-Pro-D-Ala-NH$_2$ is prepared by the solid phase procedure referred to above. Following the removal of the Fmoc protection, the peptide intermediate is reacted as generally described in Example I, but using 6-ethyl-picolinic acid to acylate the side chain amino groups of the Dpr and D-Dpr residues in the 5- and 6-positions. Following cleavage and HPLC purification as previously described, the GnRH antagonist is tested, and the peptide is considered to be effective to prevent ovulation of female mammals at low dosages.

Although the invention has been described with regard to its preferred embodiments, it should be understood that changes and modifications as would be obvious to one having the ordinary skill in this art may be made without departing from the scope of the invention which is set forth in the claims which are appended hereto. Although it is preferred to complete the solid-phase synthesis of the entire peptide before effecting the acylation reaction, if desired a fragment containing the lysine or other residues can be acylated before the synthesis of the N-terminal segment is carried out. With respect to the specific GnRH antagonists illustrated herein, other substitutions known in the art which do not significantly detract from the effectiveness of the peptides may be employed in the illustrated peptides or in peptides of other lengths made by solid-phase synthesis in accordance with the teachings of the invention. D-2PAL and D-4PAL are considered to be equivalents of D-3PAL. Substituted Phe, such as (4F)Phe, can be used instead of Phe in the 7-position. Both butyl Lys and diethyl Lys are considered to be equivalents of ILys; however, ILys is preferred. Other hydrophobic amino acid residues can also be employed in the 1-position, preferably in D-isomer form, and are considered equivalents of those specified. Such analogs can be administered in the form of their pharmaceutically or vetinarially acceptable, nontoxic salts, as indicated hereinbefore, which are considered equivalents, and thus the peptides can be appropriately optionally changed to their acid addition salts as well known in this art.

Particular features of the invention are emphasized in the claims which follow.

What is claimed is:

1. A method for making a peptide having the formula: Ac-$\beta$-D-2NAL-(4Cl)D-Phe-D-3PAL-Ser-Lys(nicotinoyl)-D-Lys(nicotinoyl)-Leu-Lys(isopropyl)-Pro-D-Ala-NH$_2$; which method comprises (a) forming a first intermediate peptide by solid phase synthesis having the formula: (N$^\alpha$Boc)-$\beta$-D-2-NAL-(4Cl)D-Phe-D-3PAL-Ser(Bzl)-Lys(Fmoc)-D-Lys(Fmoc)-Leu-Lys(2ClZ)-Pro-D-Ala-NH-[resin support], (b) deblocking the N-terminus by removal of Boc; (c) acetylating said deblocked N-terminus with a molar excess of acetic anhydride in dichloromethane; (d) removing said Fmoc protecting groups on said 5-position Lys and 6-position D-Lys; (e) acylating said deprotected amino groups by reacting with a molar excess of nicotinic acid in DMF, using DIIC as a coupling agent, resulting in a second peptide intermediate having the formula: Ac-$\beta$-D-2NAL-(4Cl)D-Phe-D-3PAL-Ser)Bzl)-Lys(nicotinoyl)-D-Lys(Nicotinoyl)-Leu-Lys(2ClZ)-Pro-D-Ala-NH-[resin support]; (f) reacting said second intermediate peptide with cyclohexane in the presence of paladium catalyst on charcoal to accomplish phase transfer hydrogenation at the 2ClZ and Bzl protecting groups; (g) reacting said deprotected second intermediate peptide with acetone in a solution of sodium borate buffer at a pH of about 9 and (h) cleaving said peptide from the resin with HF.

2. A method for making a peptide having the formula: Ac-$\beta$-D-2NAL-(4Cl)D-Phe-D-3PAL-Ser-Lys(nicotinoyl)-D-Lys(nicotinoyl)-Leu-Lys(isopropyl)-Pro-D-Ala-NH$_2$, which method comprises (a) forming a first intermediate peptide by solid phase synthesis having the formula: (N$^\alpha$Boc)-$\beta$-D-2NAL-(4Cl)D-Phe-D-3PAL-Ser(X$^3$)-Lys(Fmoc)-D-Lys(Fmoc)-Leu-Lys(2ClZ)-Pro-D-Ala-NH-[resin support], wherein X$^3$ is a protecting group for a hydroxyl group of Ser; (b) initially deblocking the N-terminus by removal of Boc; (c) acetylating said deblocked N-terminus with a molar excess of acetic anhydride; (d) then removing said Fmoc protecting groups on said 5-position Lys and 6-position D-Lys; (e) acylating said deprotected amino groups by reacting with a molar excess of nicotinic acid plus a coupling agent, resulting in a second peptide intermediate having the formula: Ac-$\beta$-D-2NAL-(4Cl)D-Phe-D-3PAL-Ser(X$^3$)-Lys(nicotinoyl)-D-Lys(Nicotinoyl)-Leu-Lys(2ClZ)-Pro-D-Ala-NH-[resin support]; (f) deprotecting said second intermediate peptide by reacting with cyclohexane in the presence of paladium catalyst on charcoal to accomplish phase transfer hydrogenation at the 2ClZ and X$^3$ protecting groups; (g) reacting said deprotected second intermediate peptide with acetone in a solution of sodium borate buffer, and (h) then cleaving said peptide from the resin support with HF.

* * * * *

UNITED STATES PATENT AND TRADEMARK OFFICE
CERTIFICATE OF CORRECTION

PATENT NO. : 5,169,935
DATED : December 8, 1992
INVENTOR(S) : Hoeger et al.

It is certified that error appears in the above-indentified patent and that said Letters Patent is hereby corrected as shown below:

On the Title page item [56] "Other Publications", Stewart et al., change "(and ed 1984)" to --(2nd ed 1984)--. Column 6, line 7, after "February" insert --11, 1986. Solid--. Column 7, line 30, change "o-amino" to --α-amino--. Column 12, line 59, after "(NaBH$_4$)" insert --.-- (period). Column 13, line 38, change "Phez$^2$" to --Phe$^2$--. Column 13, lines 52 and 63, change "Phe$^{22}$" to --Phe$^2$--. Column 14, line 5, change "Phe$^{22}$" to --Phe$^2$--. Column 14, line 16, change "2NAL:" to --2NAL$^1$--.
Claim 22, column 16, line 25, change "Ser)Bzl)" to --Ser(Bzl)--. Claim 22, column 16, line 26, change "Lys(Nicotinoyl): to --Lys(nicotinoyl)--. Claim 23, column 16, line 53, change "Lys(Nicotinoyl)" to --Lys(nicotinoyl)--.

Signed and Sealed this

Fourteenth Day of December, 1993

Attest:

BRUCE LEHMAN

Attesting Officer    Commissioner of Patents and Trademarks